(12) United States Patent
Saikalis et al.

(10) Patent No.: US 6,756,571 B2
(45) Date of Patent: Jun. 29, 2004

(54) SYSTEM AND METHOD FOR COMPENSATION OF CONTAMINATION OF A HEATED ELEMENT IN A HEATED ELEMENT GAS FLOW SENSOR

(75) Inventors: George Saikalis, West Bloomfield, MI (US); Shigeru Oho, Farmington Hills, MI (US)

(73) Assignee: Hitachi, Ltd., Tokyo (JP)

( * ) Notice: Subject to any disclaimer, the term of this patent is extended or adjusted under 35 U.S.C. 154(b) by 65 days.

(21) Appl. No.: 10/273,050

(22) Filed: Oct. 17, 2002

(65) Prior Publication Data

US 2004/0074896 A1 Apr. 22, 2004

(51) Int. Cl.[7] .............................................. H05B 1/02
(52) U.S. Cl. ................... 219/497; 73/118.2; 73/204.18; 219/205
(58) Field of Search ................................ 219/497, 202, 219/501, 205; 73/204.18, 204.19, 204.11, 204.15, 204.16, 204.23–204.27, 118.2; 123/494

(56) References Cited

U.S. PATENT DOCUMENTS

| 4,196,622 A | 4/1980 | Peter ........................... 73/204 |
| 4,264,961 A | 4/1981 | Nishimura et al. ......... 364/510 |
| 4,320,650 A | 3/1982 | Kita ................................. 73/3 |
| 4,357,829 A | 11/1982 | Kraus et al. .................... 73/204 |
| 4,505,248 A | 3/1985 | Yuzawa et al. ............. 123/519 |
| 4,522,176 A | 6/1985 | Takao et al. ................ 123/339 |
| 4,693,115 A | 9/1987 | Tokura et al. ................. 73/204 |
| 4,846,133 A | 7/1989 | Shiraishi et al. ............ 123/494 |
| 4,881,505 A | 11/1989 | Tomisawa .................... 123/480 |
| 4,944,182 A | 7/1990 | Gneiss et al. ............ 73/204.26 |
| 4,986,244 A | 1/1991 | Kobayashi et al. ......... 123/488 |
| 5,044,196 A | 9/1991 | Tomisawa et al. ......... 73/118.2 |
| 5,067,466 A | 11/1991 | Nagaishi ...................... 123/494 |
| 5,095,743 A | 3/1992 | Tomisawa ................... 73/118.1 |
| 5,199,300 A | 4/1993 | Kienzle et al. ............. 73/118.2 |
| RE34,403 E | 10/1993 | Arai et al. ................... 123/494 |
| 5,614,667 A | 3/1997 | Hosoya ...................... 73/118.2 |
| 5,918,584 A | 7/1999 | Kato ........................... 123/681 |
| 6,672,153 B2 * | 1/2004 | Igarashi et al. .......... 73/204.15 |
| 2002/0000436 A1 * | 1/2002 | Hashimoto et al. ......... 219/497 |
| 2003/0019865 A1 * | 1/2003 | Whitney et al. ............. 219/497 |
| 2004/0026408 A1 * | 2/2004 | Morinaga et al. ........... 219/497 |

FOREIGN PATENT DOCUMENTS

JP         9-304320      * 11/1997

OTHER PUBLICATIONS

"Modeling of Advanced Control Strategies for Air Flow Sensor", Saikalis et al.., IFAC 2001, Karlsruhe, Germany.

* cited by examiner

Primary Examiner—John A. Jeffery
(74) Attorney, Agent, or Firm—Gifford, Krass, Groh, Sprinkle, Anderson & Citkowski, P.C.

(57) ABSTRACT

A system for compensation of contamination of a heated element in a heated element gas flow system in which the heated element becomes heated from an ambient temperature to an elevated temperature upon the application of electrical power to the heated element during a startup time period. The system includes a processing circuit having an input and an output. A voltage signal from the heated element is connected to the input of the processing circuit. The processing circuit reads a plurality of temporally spaced input signals as data from the processing circuit input during the startup time period. The processing circuit then computes the parameters of a transfer function corresponding to the data on its input. The processing circuit then calculates a contamination correction factor as a function of at least one parameter of the transfer function. The processing circuit then utilizes the correction factor to modify a measured gas flow rate by the gas flow meter after the heated element attains the elevated steady state temperature to compensate for contamination of the heated element.

22 Claims, 6 Drawing Sheets

SYSTEM AND METHOD FOR COMPENSATION OF CONTAMINATION OF A HEATED ELEMENT IN A HEATED ELEMENT GAS FLOW SENSOR

BACKGROUND OF THE INVENTION

I. Field of the Invention

The present invention relates generally to heated element gas flow sensors and, more particularly, to a method and system for compensation of contamination of the heated element in the gas flow sensor.

II. Description of Related Art

Gas flow sensors which measure the mass gas flow are utilized in many different applications. For example, gas flow sensors are utilized in the intake manifold of automotive vehicles to measure the mass airflow through the intake manifold and into the engine. Similarly, gas flow sensors are utilized to measure the mass flow of flammable gases, such as propane and the like, in both automotive as well as other applications, such as fuel cell applications.

Many of the previously known gas flow sensors utilize a heated element to determine the gas flow rate through the sensor. When used in an automotive application, this flow rate, in conjunction with other parameters, is then coupled as an input to a fuel management system which regulates and controls the operation of the engine for improved engine performance, reduced emissions and the like.

These previously known heated element gas flow sensors utilize a resistive element which is disposed within the gas flow path of the sensor. A control circuit varies the current flow through the resistive element by an amount sufficient to maintain the temperature differential between the resistive element and ambient air temperature at a predetermined constant, typically 200° centigrade. The magnitude of current through the resistive element is then proportional to the gas flow rate through the flow sensor.

While these gas flow sensors accurately determine the gas flow rate through the sensor when the gas flow sensor is relatively new, after prolonged use, the heated element may be subjected to contaminants of one sort or another. For example, when the gas flow sensor is utilized in the intake manifold of an automotive engine, the heated element is subjected to dirt, dust, oil and other debris in the air stream inducted through the gas flow sensor. After prolonged use, this debris can and does adhere to the outer surface of the heated element.

When the heated element becomes increasingly covered with debris and other contaminants, the thermal capacitance of the heated element increases. This increase in thermal capacitance, furthermore, results in an inaccurate output signal from the gas flow sensor. Such an inaccurate signal, in turn, may result in poor engine performance, increased emissions and other undesirable effects.

SUMMARY OF THE PRESENT INVENTION

The present invention provides both a method and system for compensation of contamination of a heated element in a heated element gas flow sensor which identifies not only the degree of contamination of a heated gas flow sensor, but also compensates for this contamination to provide a more accurate signal to the fuel management system of the engine and thereby enhance engine performance and achieve low emissions.

In brief, the system of the present invention provides for compensation of contamination of a heated element of the type where the heated element and a cold element are disposed within the gas flow. Upon engine startup, electrical power is applied to the heated element so that the heated element rises in temperature from an ambient temperature and to an elevated temperature during a startup period. Once the heated element achieves its elevated temperature, typically 200° centigrade above ambient temperature, a control circuit for the heated element gas flow sensor maintains the temperature differential between the heated element and the cold element of the gas flow sensor at a constant value by varying the current through the heated element. The magnitude of the current flow through the heated element is thus proportional to the gas flow rate through the flow meter.

The system of the present invention includes a processing circuit having an input and an output. A voltage signal from the heated element is connected to the processing circuit input. Preferably, the processing circuit comprises a microprocessor based processing circuit.

Means in the processing circuit then read a plurality of temporally spaced signals corresponding to the temperature of the heated element as data from the input to the processing circuit during the startup time period. Typically, this data forms a curve having a defined slope as the heated element becomes heated from an ambient gas temperature and to the elevated steady state operating temperature.

The processing circuit is programmed to compute parameters of a transfer function corresponding to the data. Preferably, this transfer function is a second order transfer function and is computed on a real time basis during the startup time period following the application of electrical power to the heated element using an adaptive algorithm.

After the processing circuit computes the transfer function parameters the processing circuit determines a contamination correction factor as a function of at least one parameter of the transfer function. In practice, the slope of the transfer function parameter constitutes the most important factor of the transfer function and this slope is then utilized by the processing circuit to generate the correction factor. The processing circuit then utilizes the correction factor to modify the measured gas flow rate by the gas flow meter after the heated element attains the elevated steady state temperature to compensate for contamination of the heated element.

BRIEF DESCRIPTION OF THE DRAWING

A better understanding of the present invention will be had upon reference to the following detailed description, when read in conjunction with the accompanying drawing, wherein like reference characters refer to like parts throughout the several views, and in which.

DETAILED DESCRIPTION OF A PREFERRED EMBODIMENT OF THE PRESENT INVENTION

Figure 1:
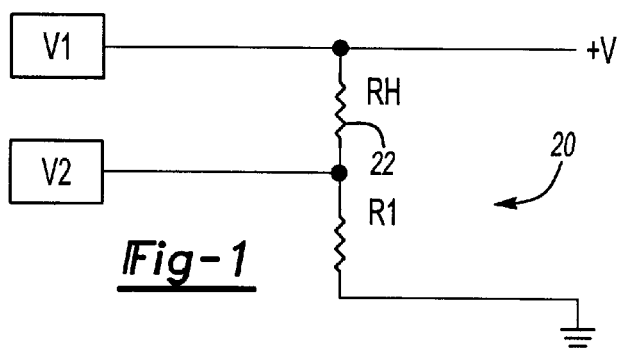
FIG. 1 is a simplified schematic view illustrating a heated element gas flow sensor.

With reference now to FIG. 1, the gas flow sensor 20 of the type used in automotive applications is illustrated and includes a housing 200 having a throughbore 202 connected in series with the intake air passageway or intake manifold of the engine. A bypass tube 204 is mounted in the housing 200 so that a predetermined portion of the gas flow through the housing throughbore 202 passes through the bypass tube 204.

Both a heated element 22 and a cold element 208 are mounted in the bypass tube 204. During a steady state operating condition, conventional control circuitry 210 (illustrated only diagrammatically) maintains the temperature differential between the heated element 22 and cold element 208 at a constant temperature, typically 200° C., so that the current through the heated element 22 is proportional to the mass gas flow through the housing throughbore 202.

With reference now to FIG. 1, a partial schematic view of the gas flow sensor 20 is shown having the heated element 22 connected in series with a resistor $R_1$ between a source of electrical power +V and ground. Furthermore, the temperature of the heated element 22 is determined from the following formula:

$$T_h = \frac{1}{\alpha}\left(\frac{(V1-V2)}{V2} \cdot \frac{R_1}{R_0} - 1\right)$$

Where: $R_0$: Resistance of hot wire at 0° C.

$R_1$: Resistance of $R_1$ $\alpha$: 0.00387 ppm/° C.

$T_h$: Temperature of heated element

Figure 2:
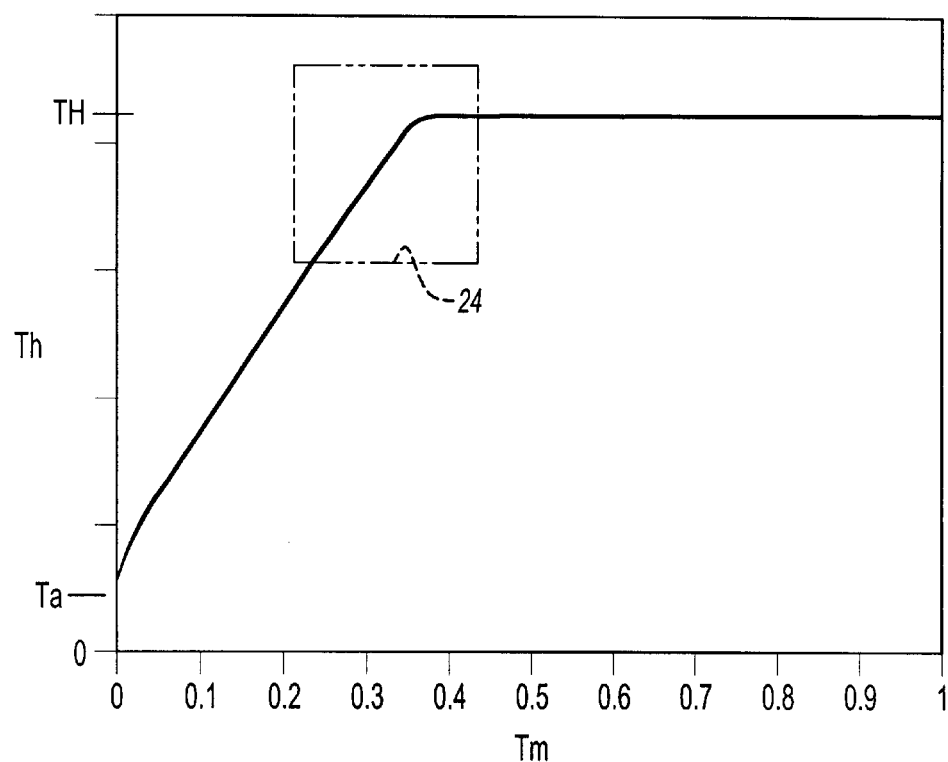
FIG. 2 is a graph illustrating the temperature $T_h$ of the heated element of a gas flow sensor during the warm up period of the heated element.
Figure 3:
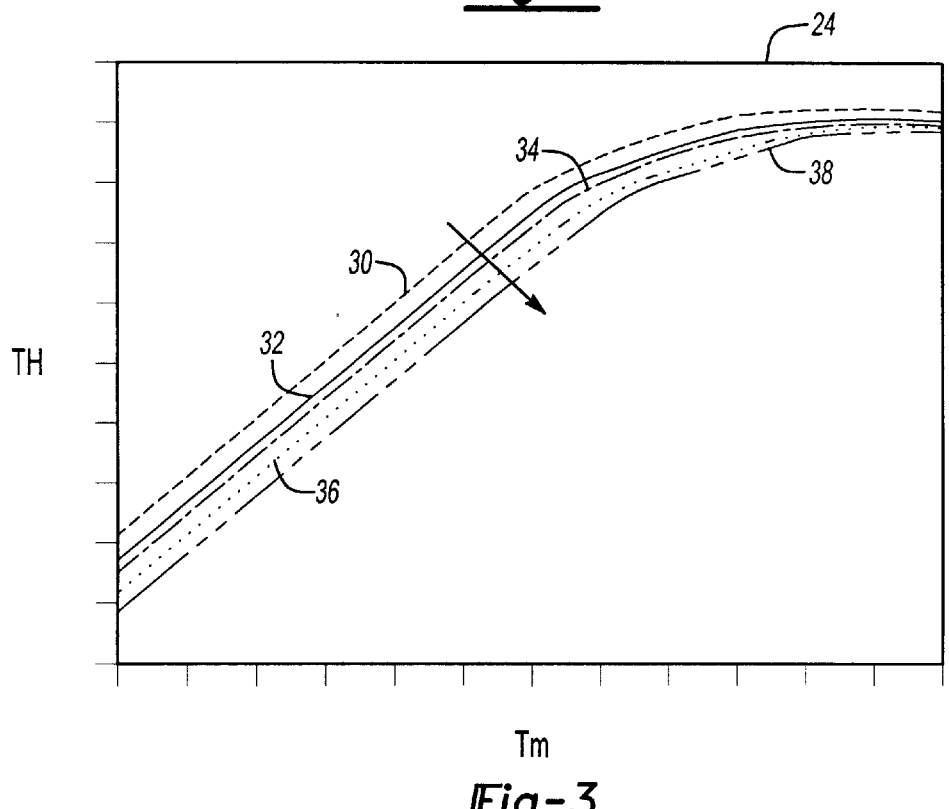
FIG. 3 is a graph of block 24 in FIG. 2 and enlarged for clarity.
Figure 11:
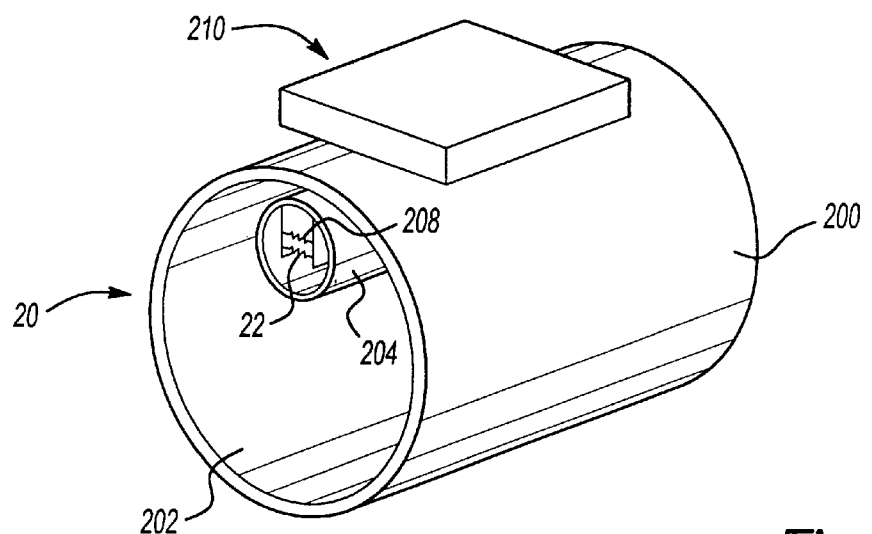
FIG. 11 is a view of a typical automotive heated element gas sensor.

With reference now to FIGS. 2 and 3, the temperature of the heated element 22 becomes heated from an ambient temperature $T_a$ (FIG. 2) to an elevated steady state operating temperature $T_H$ during a startup time period $t_m$. This exemplary startup time period $t_m$ is illustrated in FIG. 2 as just under 400 milliseconds. Once the heated element 22 attains its operating temperature $T_H$, the control circuit 210 (FIG. 11) maintains the constant temperature differential between the heated element 22 and cold element 208.

A portion 24 of the graph of the heated element temperature $T_h$ during the startup period $t_m$ is shown and enlarged in FIG. 3 which shows a number of graphs of the temperature $T_h$ of the hot wire 22 with varying degrees of contamination. For example, the graph 30 illustrates the heated element 22 in a clean, uncontaminated condition. Conversely, the graph 32 illustrates the temperature $T_h$ of the heated element 22 when the heated element 22 has slight contamination. Similarly, graphs 34 all disclose the temperature $T_h$ of the heated element 22 with increasing degrees of contamination of the heated element 22. Furthermore, the temperature $T_h$ of the heated element is substantially linear during most of time $t_m$.

Thus, it is clear from FIG. 2, as the contamination of the heated element 22 increases, the slope of the temperature $T_h$ of the hot wire versus time during the startup period $t_m$ decreases. As such, the slope of each graph 32–38 is, itself, an indication of the degree of contamination of the heated element 22.

Figure 4:
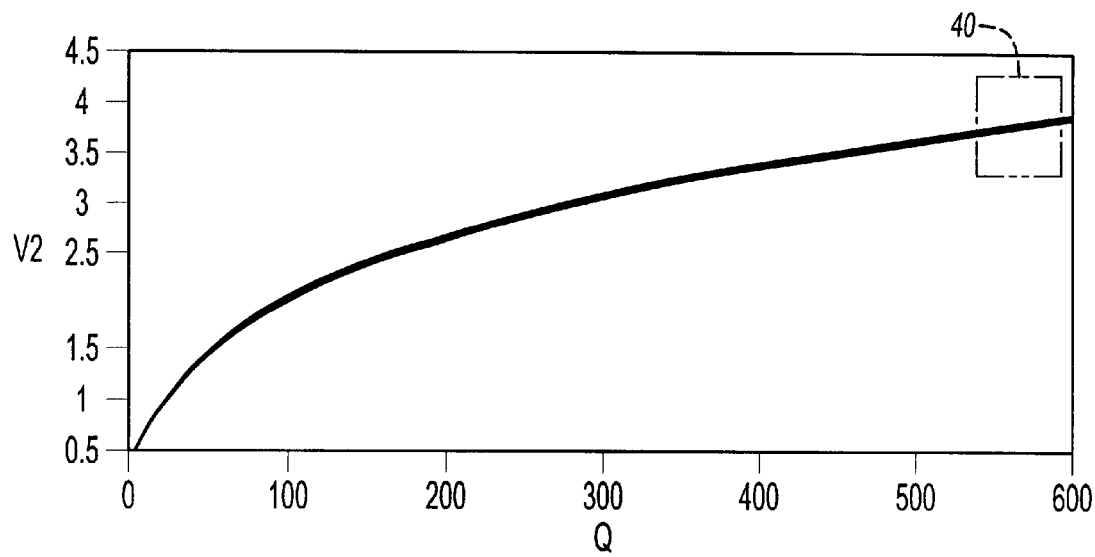
FIG. 4 is a graph illustrating the output voltage $V_2$ from the gas flow sensor as a function of gas flow rate and illustrating different levels of contamination of the heated element.
Figure 5:
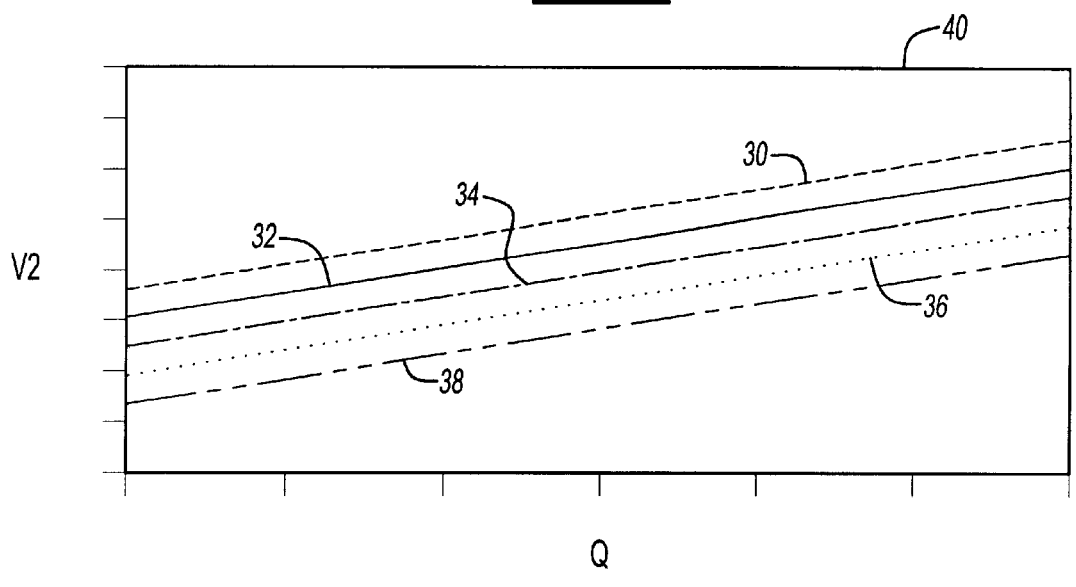
FIG. 5 is an enlarged view of block 40 of FIG. 4.

The error or difference between the graphs 30–38 as contamination increases is not, however, limited merely to the startup time period $t_m$. Rather, as shown in FIGS. 4 and 5, the error in the output signal $V_1$ from the gas flow sensor 20 also increases with the increase of the gas flow rate even after the heated element 22 of the gas flow sensor 20 reaches its operational steady state temperature. For example, as best shown in FIG. 5, the graphs 30–38 from box 40 in FIG. 4 clearly depict a different output signal $V_1$ from the gas flow sensor 20 which decreases at a given airflow velocity as a function of the degree of contamination of the heated element 22.

Figure 6:
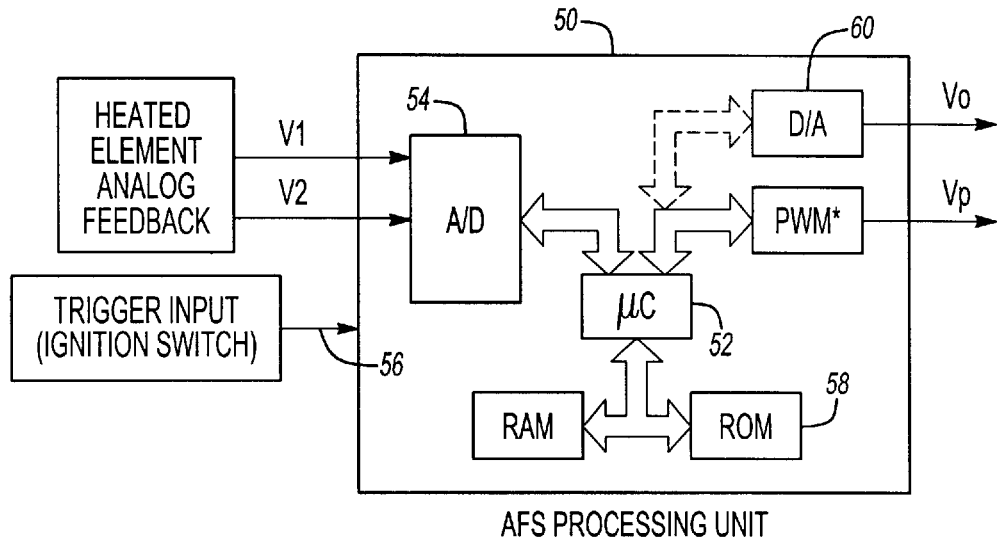
FIG. 6 is a block view illustrating a first preferred embodiment of the present invention.

With reference now to FIG. 6, a first preferred embodiment of the system 50 to compensate for contamination of the heated element is shown and includes a microprocessor 52. The input signals $V_1$ and $V_2$ (FIG. 1) from the gas flow sensor 20 are coupled as input signals to the microprocessor 52 through an analog/digital converter 54. The microprocessor 52 also receives as an input signal a trigger input 56 which corresponds to the initial application of electrical power +V to the heated element 22. For example, the trigger input 56 may correspond to activation of the engine ignition switch.

Still referring to FIG. 6, the microprocessor 52, under programmed control from a program stored in digital memory 58, modifies the output signal $V_2$ from the gas flow sensor 20 to compensate for contamination of the heated element 22 in a fashion which will be subsequently described in greater detail. The microprocessor 52 then outputs the signal through a digital/analog converter 60 as an output $V_o$ modified to compensate for contamination of the heated element 22. Optionally, the microprocessor 52 provides a signal as a pulse width modified signal $V_p$ in lieu of or in addition to the analog signal $V_o$.

Figure 7:
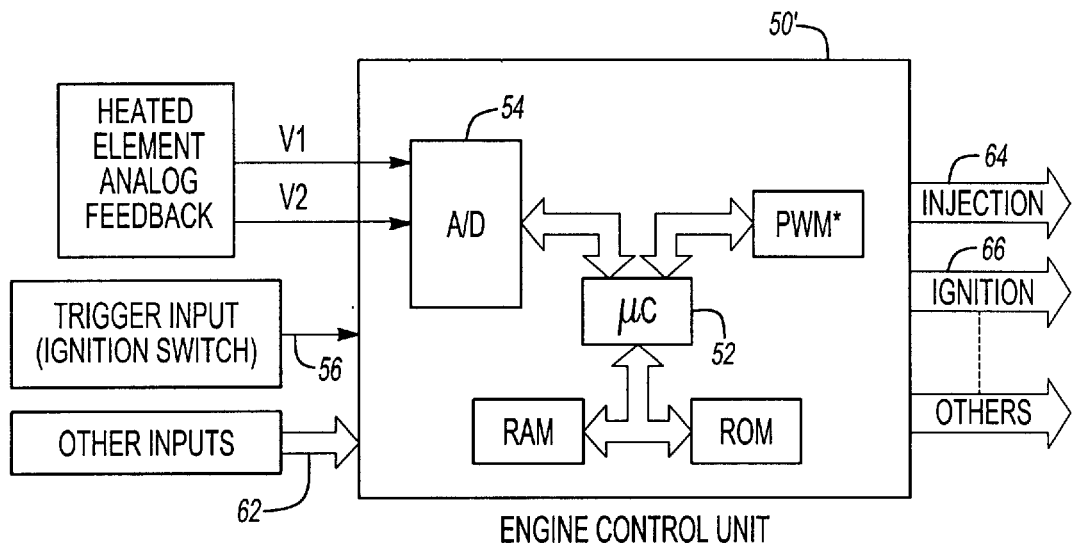
FIG. 7 is a block view similar to FIG. 6, but illustrating a modification thereof.

With reference now to FIG. 7, a modification of the system 50' of the present invention is shown in which the signals $V_1$ and $V_2$ from the gas flow sensor 20 are also coupled as input signals through the A/D converter 54 to the microprocessor 52. The trigger input 56 is also connected as an input signal to the microprocessor 52 whereas other inputs 62 relating to various engine parameters are also coupled as input signals to the microprocessor 52.

Unlike the system 50 illustrated in FIG. 6, however, the microprocessor 52 in the system 50' of FIG. 7 is programmed to not only compensate for contamination of the heated element 22 in a fashion to be subsequently described in greater detail, but is also programmed to control both the engine fuel injection on output line 64 as well as ignition of the engine spark plugs on line 66. Thus, unlike the embodiment illustrated in FIG. 6, the system 50' of FIG. 7 integrates the heated element contamination compensation with the fuel management of the entire engine into a single system.

Figure 8:
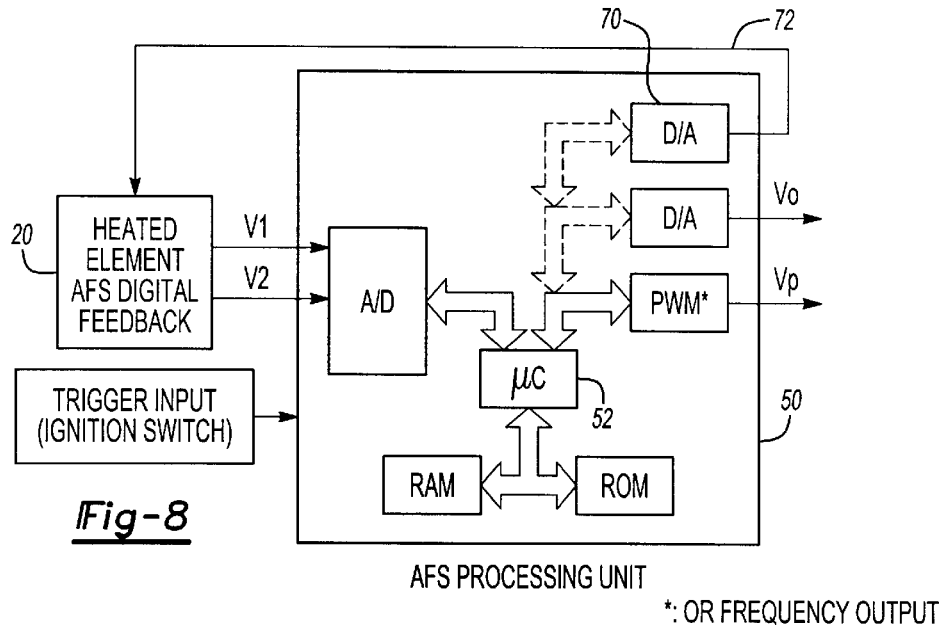
FIG. 8 is a block view similar to FIGS. 6 and 7 and illustrating still a further modification thereof.

It will also be understood that the system 50 of FIG. 6 as well as the system 50' of FIG. 7 both utilize an analog feedback for the heated element gas flow sensor in order to maintain the differential between the heated element and the cold element at the target differential, typically 200° centigrade. However, as shown in FIG. 8, in a modified system 50'', the microprocessor 52 through a D/A converter 70 provides digital feedback on line 72 to control the operation of the gas flow sensor 20.

As previously discussed with respect to FIGS. 2 and 3, the behavior slope e.g., of the temperature $T_h$ of the heated element 22 varies with the degree of the contamination of the heated element 22 during the initial startup period. Consequently, the determination of the slope of the temperature $T_h$ of the heated element 22 during the electrical energization and warm up of the heated element 32 provides a fairly direct correlation of the degree of contamination of the heated element 22.

In order to calculate an equation corresponding to a curve fit of the data points of the temperature $T_h$ of the heated element 22 during the startup period $t_m$, preferably a transfer function in the following form is utilized:

$$G(s) = \frac{b_n s^{n-1} + \ldots + b_2 s + b_1}{s^n + a_n s^{n+1} + \ldots + a_2 s + a_1}$$

Although the accuracy of the transfer function G(s) increases with an increase of the order n, a second order transfer function G(s) is sufficient to adequately derive a curve of the temperature $T_h$ of the heated element 22 during the warm up period $t_m$. As such, the above transfer equation reduces to the following:

$$G(s) = \frac{b_2 s + b_1}{s^2 + a_2 s + a_1}$$

where the transfer parameters $a_1$, $a_2$, $b_1$ and $b_2$ define the curve fit equation. Furthermore, the parameter $a_1$ corresponds to the behavior of the transient temperature $T_h$ of the heated element 22 during the warm up period $t_m$.

Although preferably a second order transfer function G(s) is utilized to determine the equation corresponding to the slope of the temperature $T_h$ during the warm up period $t_m$, any other conventional curve fitting routine may be alternately used.

Although any conventional algorithm may be employed to determine the parameters $a_1$, $a_2$, $b_1$ and $b_2$ of the transfer function G(s), preferably the transfer function parameters are determined during the time period $t_m$ on a real time basis using an adaptation algorithm. Such an adaptation algorithm is described more fully in *Advances in Automotive Control 2001: Modelling of Advanced Control Strategies for Airflow Sensor*, Proceeding 3rd IFAC Workshop—Germany ISBN: 0-080-43678-1, Elsevier Publisher, which is incorporated herein by reference. Regardless of the algorithm utilized to determine the parameters of the transfer function, at the end of time $t_m$, the parameters $a_1$–$b_2$ of the transfer function are identified. Of these, the parameter $a_1$ corresponding to the slope of the temperature $T_h$ in FIG. 2 is the most critical.

Figure 9:
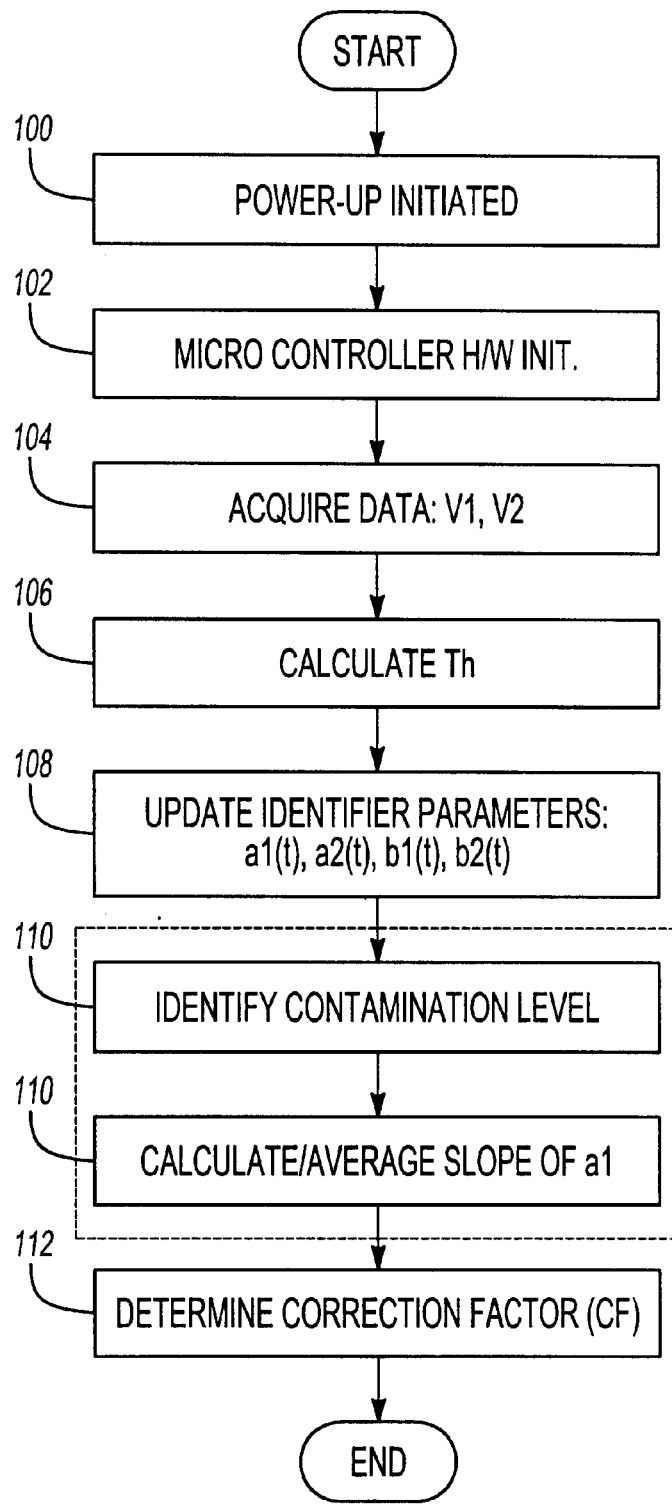
FIG. 9 is a flowchart illustrating the operation of the present invention during the warm up period for the heated element of the gas flow sensor.

With reference now to FIG. 9, a flowchart illustrating the operation of the system of the present invention is shown. Furthermore, the flowchart illustrated in FIG. 9 assumes that the heated element 22 (FIG. 1) is initially at ambient temperature.

At step 100 electrical power is applied to the heated element 22 thus corresponding to time to in FIG. 2. Such initiation of the power to the heated element 22 would occur upon ignition of the internal combustion engine when the gas flow sensor is utilized with an internal combustion engine. Step 100 then proceeds to step 102. At step 102 the microprocessor 52 (FIGS. 6–8) performs any required initialization. Such initialization varies in time depending upon the microprocessor 52, but typically is less than 100 milliseconds. Step 102 then proceeds to step 104.

At step 104, the microprocessor 52 inputs the data $V_1$ and $V_2$ (FIG. 1) from the gas flow sensor 20 and then proceeds to step 106 where the microprocessor 52 calculates the hot wire temperature $T_h$ in accordance with the formula:

$$T_h = \frac{1}{\alpha}\left(\frac{(V1 - V2)}{V2} \cdot \frac{R_1}{R_0} - 1\right)$$

Where: $R_0$: Resistance of hot wire at 0° C.

$\alpha$: 0.00387 ppm/° C.

$T_h$: Temperature of heated element.

Step 106 then proceeds to step 108.

At step 108 the microprocessor updates the parameters $a_1$, $a_2$, $b_1$ and $b_2$ of the transfer function G(s) preferably on a real time basis utilizing an adaptive algorithm. Furthermore, steps 104, 106 and 108 iterate during the entire warm up period $t_m$ of the heated element 22.

After the heated element 22 reaches its operational temperature at time $t_m$, typically between 300 milliseconds and 400 milliseconds, step 108 proceeds to step 110 where the contamination level of the heated element 22 is determined as a function of the slope $a_1$ of the transfer function G(s). Preferably the degree of contamination is determined from empirically derived lookup tables. The other parameters $a_2$, $b_1$ and $b_2$ of the transfer function G(s) may vary as a function of the contamination but are preferably disregarded as insignificant. Step 110 then proceeds to step 112.

At step 112, the microprocessor 52 determines a correction factor CF which varies as a function of the amount of contamination of the contamination of the heated element 22.

After the correction factor CF has been calculated, the correction factor CF is applied to the measured airflow Q from the heated element 22 after the heated element 22 reaches its steady state temperature, i.e. after the warm up period time $t_m$ (FIG. 3). Furthermore, in determining the correction factor CF, the slope $a_1$ for the transfer function G(s) is compared by the microprocessor with a previously stored value of the slope of the curve of the temperature curve of an uncontaminated heated element during the warm up period $t_m$. Since the slope of the temperature of the heated element $T_h$ during the warm up period $t_m$ decreases with increasing contamination of the heated element 22 as shown in FIGS. 2 and 3, the determination of the slope $a_1$ of the transfer function G(s) and its comparison with a base slope $a_1$ for an uncontaminated heated element 22 provides a correction factor CF which varies as a function of the contamination of the heated element 22.

Any conventional means may be utilized to establish the base slope $a_1$ for an uncontaminated flow sensor. For example, assuming the flow sensor is employed in an automotive vehicle, the base slope $a_1$ may be set to a predetermined value at the place of manufacture where the flow sensor is uncontaminated by usage. Such value for a, may be empirically determined.

Alternatively, the base slope $a_1$ may be established by the microprocessor 52 during the initial operation of the automotive vehicle. For example, the microprocessor 52 may determine the base slope $a_1$ during the first twenty engine start ups and then compute an average value of $a_1$ for the base slope $a_1$.

Once the correction factor CF has been determined, the correction factor CF is then applied to the measured gas flow Q from the gas flow sensor 20 after the heated element 22 reaches its operational temperature, i.e. after the warm up period $t_m$. The corrected gas flow rate $Q_{comp}$ is determined in accordance with the following equation:

$$Q_{comp} = f(Q, CF)$$
$$= d_0 + d_1 \cdot Q$$

where: Q=measured gas flow rate
$d_0 = f(a_{1base}, a_{1now}, k_0)$
$d_1 = f(a_{1base}, a_{1now}, k_1)$
$a_{1base}$=slope of an uncontaminated heated element
$a_{1now}$ slope $a_1$ of G(s)
$k_0$=constant (empirically determined)
$k_1$=constant (empirically determined)

From the above equation, it can be seen that the corrected gas flow rate $Q_{comp}$ varies as a function of the correction factor which includes the parameters $d_0$ and $d_1$. Furthermore, the actual parameters $d_0$ and $d_1$ are determined as a comparison of the slope $a_1$ of the transfer function G(s) determined during time $t_m$ and its comparison with a base slope $a_1$ for an uncontaminated heated element 22. The parameters $k_0$ and $k_1$ are empirically determined for the particular gas flow meter 20.

Figure 10:
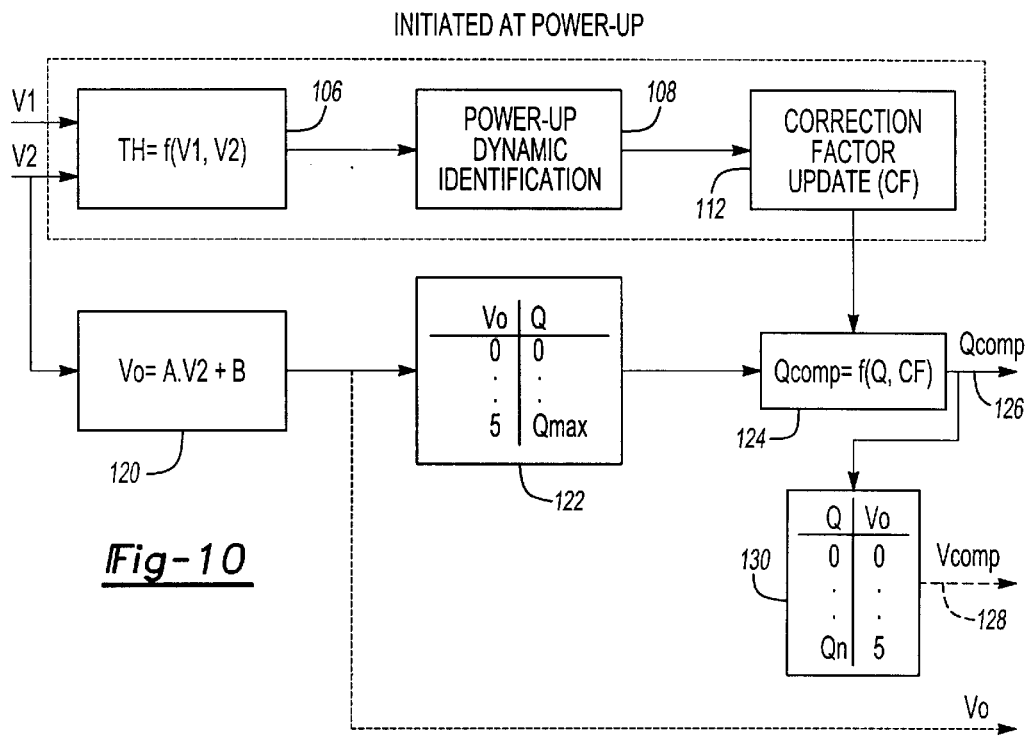
FIG. 10 is a flowchart illustrating the operation of the present invention after warm up of the heated element.

With reference now to FIG. 10, a signal processing flowchart is shown illustrating the operation of the present invention after the warm up period $t_m$, during steady state operating conditions.

In FIG. 10, the voltages $V_1$ and $V_2$ from the gas flow sensor 20 are inputted by the microprocessor at step 106 and the parameters of the transfer function G(s) are determined as previously described during the warm up period $t_m$ at step 108. The correction factor 112 is then determined at step 112 at the end of the warm up period $t_m$.

The voltage $V_2$, i.e. the voltage output signal from the gas flow sensor 20, is also coupled as an input signal to a block 120 which provides a corrected output signal $V_o$ after trimming the output signal $V_2$ from the gas flow sensor 20 in the conventional fashion. $V_o$ can be accomplished in either hardware or software.

The trimmed output signal $V_o$ from the block 120 is then utilized by the microprocessor in connection with a lookup table 122 to determine the gas flow rate corresponding to the output voltage $V_o$. This output voltage $V_o$ is not corrected for contamination of the heated element but rather merely generates an output flow signal Q corresponding to the voltage $V_o$.

At step 124 the microprocessor receives the uncompensated or measured gas flow Q from step 122 as well as the correction factor CF from step 112. Step 124 then calculates the compensated gas flow rate $Q_{comp}$ as a function of both the measured gas flow rate Q and the correction factor CF in the previously described fashion. The microprocessor then outputs this compensated gas flow rate $Q_{comp}$ on its output line 126. The output signal on line 126 is then used in any conventional fashion, such as by the fuel and ignition management system of an internal combustion engine, flow management system of a fuel cell, or the like.

Still referring to FIG. 10, optionally the microprocessor also utilizes the compensated output signal $Q_{comp}$ on line 126 to output a compensated voltage signal $V_{comp}$ on line 128. A lookup table 130 is preferably used by the microprocessor to determine the value of the compensated voltage signal $V_{comp}$. The compensated voltage signal $V_{comp}$ may be used, for example, by external microprocessors through conventional A/D converters.

From the foregoing, it can be seen that the present invention provides both a system and method for compensation of contamination of the heated element of a gas flow sensor. By such compensation of the output signal from the gas flow sensor, reduced emissions, better engine economy, operation and efficiency of an internal combustion engine as well as other applications are achieved despite contamination of the heated element of the gas flow sensor.

Having described my invention, however, many modifications thereto will become apparent to those skilled in the art to which it pertains without deviation from the spirit of the invention as defined by the scope of the appended claims.

We claim:

1. A system for compensation of contamination of a heated element in a heated element gas flow sensor, said heated element becoming heated from an ambient temperature to an elevated temperature upon application of electrical power to the heated element during a startup time period, said system comprising:
   a processing circuit having an input and an output, a voltage signal from the heated element being connected to said processing circuit input,
   means in said processing circuit which reads a plurality of temporally spaced signals as data from said processing circuit input during the startup time period,
   means in said processing circuit which computes parameters of a transfer function corresponding to said data,
   means in said processing circuit which calculates a contamination correction factor as a function of at least one parameter of said transfer function, said processing circuit utilizing said correction factor to modify a measured gas flow rate by the gas flow meter after the heated element attains the elevated temperature to compensate for contamination of the heated element.

2. The invention as defined in claim 1 wherein said processing means comprises a microprocessor.

3. The invention as defined in claim 2 wherein said means for computing the transfer function further comprises said microprocessor applying an adaptive algorithm to said data.

4. The invention as defined in claim 1 wherein said means for computing the transfer function comprises means for computing the transfer function on a real time basis during the startup period.

5. The invention as defined in claim 1 wherein said means for computing the transfer function comprises means for computing a second order transfer function.

6. The invention as defined in claim 1 wherein said at least one parameter of said transfer function comprises a parameter corresponding to a behavior of the transfer function.

7. The invention as defined in claim 1 wherein said correction factor comprises a first computed value plus a second computed value multiplied by the measured gas flow.

8. The invention as defined in claim 1 wherein said gas flow sensor comprises an automotive gas flow sensor.

9. A method for compensation of contamination of a heated element in a heated element gas flow sensor, said heated element becoming heated from an ambient temperature to an elevated temperature upon application of electrical power to the heated element during a startup time period, said method comprising the steps of:
   inputting a plurality of temporally spaced voltage signals as data from the heated element during the startup time period,
   computing parameters of a transfer function corresponding to said data,
   calculating a contamination correction factor as a function of at least one parameter of said transfer function, and
   utilizing said correction factor to modify a measured gas flow rate by the gas flow meter after the heated element attains the elevated temperature to compensate for contamination of the heated element.

10. The invention as defined in claim 9 wherein said computing the transfer function step further comprises the step of applying an adaptive algorithm to said data.

11. The invention as defined in claim 9 wherein said computing the transfer function step comprises the step of computing the transfer function on a real time basis during the startup period.

12. The invention as defined in claim 9 wherein said computing the transfer function step comprises the step of computing a second order transfer function.

13. The invention as defined in claim 9 wherein said at least one parameter of said transfer function comprises a parameter corresponding to a behavior of the transfer function.

14. The invention as defined in claim 9 wherein said correction factor comprises a first computer value plus a second computer value multiplied by the measured gas flow.

15. A system for compensation of contamination of a heated element in a heated element gas flow sensor, said heated element becoming heated from an ambient temperature to an elevated temperature upon application of electrical power to the heated element during a startup time period, said system comprising:

a programmed processing circuit having an input and an output, a voltage signal from the heated element being connected to said processing circuit input, programmed means in said processing circuit for reading a plurality of temporally spaced signals as data from said processing circuit input during the startup time period, programmed means in said processing circuit for computing parameters of a transfer function corresponding to said data, programmed means in said processing circuit for comparing said transfer function with a previous stored transfer function representative of the voltage at the heated element during the startup time period when the heated element is in a less contaminated state and for calculating a contamination correction factor as a function of at least one parameter of said transfer function, said processing circuit utilizing said correction factor to modify a measured gas flow rate by the gas flow meter after the heated element attains the elevated temperature to compensate for contamination of the heated element.

16. The invention as defined in claim 15 wherein said processing means comprises a microprocessor.

17. The invention as defined in claim 16 wherein said means for computing the transfer function further comprises said microprocessor applying an adaptive algorithm to said data.

18. The invention as defined in claim 15 wherein said means for computing the transfer function comprises means for computing the transfer function on a real time basis during the startup period.

19. The invention as defined in claim 15 wherein said means for computing the transfer function comprises means for computing a second order transfer function.

20. The invention as defined in claim 15 wherein said at least one parameter of said transfer function comprises a parameter corresponding to a behavior of the transfer function.

21. The invention as defined in claim 15 wherein said correction factor comprises a first computer value plus a second computed value multiplied by the measured gas flow.

22. The invention as defined in claim 15 wherein said gas flow sensor comprises an automotive gas flow sensor.

* * * * *